United States Patent
Lee et al.

(10) Patent No.: US 7,169,110 B2
(45) Date of Patent: Jan. 30, 2007

(54) APPARATUS AND METHOD FOR DIAGNOSING SLEEP APNEA

(75) Inventors: Jong-youn Lee, Yongin-si (KR); Gil-won Yoon, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 315 days.

(21) Appl. No.: 10/830,113

(22) Filed: Apr. 23, 2004

(65) Prior Publication Data

US 2004/0215095 A1    Oct. 28, 2004

(30) Foreign Application Priority Data

Apr. 25, 2003 (KR) ............... 10-2003-0026396

(51) Int. Cl.
*A61B 5/08* (2006.01)
(52) U.S. Cl. .............. 600/484; 600/481; 600/483; 600/500; 600/529
(58) Field of Classification Search .......... 600/481, 600/483, 484, 500, 529–542
See application file for complete search history.

(56) References Cited

U.S. PATENT DOCUMENTS

| | | | | |
|---|---|---|---|---|
| 3,799,672 | A * | 3/1974 | Vurek ............ | 356/41 |
| 4,651,741 | A | 3/1987 | Passafaro | |
| 4,765,340 | A | 8/1988 | Sakai et al. | |
| 4,800,495 | A * | 1/1989 | Smith ............ | 600/322 |
| 4,819,752 | A * | 4/1989 | Zelin ............ | 600/322 |
| 5,385,144 | A * | 1/1995 | Yamanishi et al. .... | 600/330 |
| 5,396,893 | A | 3/1995 | Oberg et al. ........ | 128/671 |
| 5,398,682 | A | 3/1995 | Lynn | |
| 5,588,425 | A * | 12/1996 | Sackner et al. ....... | 600/523 |
| 6,047,203 | A | 4/2000 | Sackner et al. ....... | 600/388 |
| 6,172,743 | B1 | 1/2001 | Kley et al. | |
| 6,342,039 | B1 | 1/2002 | Lynn et al. ......... | 600/529 |
| 6,368,287 | B1 | 4/2002 | Hadas ............. | 600/529 |
| 6,415,174 | B1 | 7/2002 | Bebehani et al. ..... | 600/513 |
| 6,811,538 | B2 * | 11/2004 | Westbrook et al. .... | 600/529 |
| 6,997,879 | B1 * | 2/2006 | Turcott ............ | 600/507 |

FOREIGN PATENT DOCUMENTS

| | | |
|---|---|---|
| EP | 0 335 356 A2 | 10/1989 |
| EP | 0 335 356 A3 | 10/1989 |

(Continued)

*Primary Examiner*—Charles A Marmor, II
*Assistant Examiner*—Zoe E Baxter
(74) *Attorney, Agent, or Firm*—Lee & Morse, P.C.

(57) ABSTRACT

An apparatus for diagnosing sleep apnea, which detects a temporary cessation of breathing during sleep by applying light to a part of a subject's body and processing light output therefrom, includes a light source unit for sequentially generating light of at least two different wavelengths according to a control signal, a photodetecting unit for detecting the light, which are generated by the light source unit and applied to the body part, and for converting the detected light signals into electric signals, a diagnosis unit for substantially removing a time delay between the electric signals output from the photodetecting unit, for calculating a ratio between the electric signals, and for comparing the ratio with a predetermined reference value to diagnose sleep apnea, and a controller for outputting the control signal to the light source unit to generate the light signals, and for providing the predetermined reference value to the diagnosis unit.

19 Claims, 4 Drawing Sheets

FOREIGN PATENT DOCUMENTS

| | | |
|---|---|---|
| JP | 61-228831 | 10/1986 |
| JP | 63-5729 | 1/1988 |
| JP | 04-022339 | 1/1992 |
| KR | 10-0340240 | 6/2002 |
| WO | WO 99/63883 | 12/1999 |

\* cited by examiner

APPARATUS AND METHOD FOR DIAGNOSING SLEEP APNEA

BACKGROUND OF THE INVENTION

1. Field of the Invention

The present invention relates to an apparatus and method for diagnosing sleep apnea. More particularly, the present invention relates to an apparatus and method for detecting whether a temporary absence or cessation of breathing occurs while a subject is sleeping by applying light of two different wavelengths to a predetermined part of the subject's body.

2. Description of the Related Art

Sleep apnea is a temporary absence or cessation of breathing during sleep, thereby causing oxygen to cease entering the body. In general, when no oxygen enters the body due to sleep apnea, an oxygen saturation, i.e., an amount of oxygen in the blood, decreases to an abnormal level.

Sleep fragmentation at night due to sleep apnea causes excessive daytime sleepiness (EDS) and a decline in arterial oxygen saturation. A decline in oxygen saturation may cause high blood pressure, arrhythmia, or the like. Occasionally, a decline in oxygen saturation may even have fatal results by causing a heart attack while a person is sleeping. It is reported that about 20 percent of the adult population of the United States suffers from snoring, and about 50 percent of those people that snore suffer from sleep apnea.

Children with sleep apnea show such symptoms as decreased attention span, erratic behavior, EDS, irregular sleep, rib cage retraction, and flaring of the ribs. Such children may do poorly in an academic setting and, in the most serious cases, may suffer from mental or psychological disorders. For infants or babies, sleep apnea may cause sudden death during sleep.

Sleep apnea is typically classified into three main types: obstructive, central, and mixed. Obstructive sleep apnea is the most common form of sleep apnea and is characterized by a repeated closing of an upper airway. Central sleep apnea occurs when the brain fails to send adequate signals to the diaphragm and lungs during sleep, thereby resulting in decreased respiration. Mixed sleep apnea is a combination of obstructive sleep apnea and central sleep apnea. Regardless of the type of sleep apnea, sleep apnea results in a decrease in arterial oxygen saturation.

A breathing disorder is clinically classified as sleep apnea when a cessation of breathing lasting for ten or more seconds occurs at least five times an hour or at least thirty times during in a seven-hour period. Snoring is a sound made when a soft palate of the upper airway vibrates, and thus, is often a direct precursor of sleep apnea.

A sleep apnea test is generally performed through polysomnography. Polysomnography is a test during which sleep architecture and function and behavioral events during sleep are objectively measured and recorded. More specifically, a number of physiological variables, such as brain waves, eye movement, chin electromyogram, leg electromyogram, electrocardiogram, snoring, blood pressure, breathing, and arterial oxygen saturation, are measured extensively. At the same time, behavioral abnormalities during sleep are recorded with video tape recorders. Trained technicians and sleep specialists read the record to obtain comprehensive results about the severity of snoring, whether arrhythmia occurs, whether blood pressure increases, whether other problems are caused during sleep, and at what points the record differs from normal sleep patterns.

Conventional apparatuses and methods for diagnosing sleep apnea have several disadvantages including being difficult to implement, being unable to detect all three types of sleep apnea, being unable to provide accurate and reliable results, and causing discomfort in a subject being monitored.

SUMMARY OF THE INVENTION

The present invention is therefore directed to an apparatus and method for diagnosing sleep apnea by measuring photoplethysmography (PPG) using light of two different wavelengths and calculating a ratio between the two measured values, which substantially overcomes one or more of the problems due to the limitations and disadvantages of the related art.

According to a feature of an embodiment of the present invention, there is provided an apparatus for diagnosing sleep apnea, which detects a temporary cessation of breathing while a subject is sleeping by applying light to and processing light output from a predetermined part of a subject's body, the apparatus including a light source unit for sequentially generating a first light signal of a first wavelength and a second light signal of a second wavelength according to a predetermined control signal, the first wavelength and the second wavelength being different, a photodetecting unit for detecting the first and second light signals output by the light source unit and then applied to the predetermined part of the subject's body, and for converting the detected first and second light signals into first and second electric signals, a diagnosis unit for substantially removing a time delay between the first and second electric signals output from the photodetecting unit, for calculating a ratio between the first and second electric signals, and for comparing the ratio with a predetermined reference value to diagnose sleep apnea, and a controller for outputting the predetermined control signal to the light source unit to generate the first and second light signals, and for providing the predetermined reference value to the diagnosis unit.

The light source unit may be a light emitting diode (LED) array that generates light in at least a red wavelength range and an infrared (IR) wavelength range. The light source unit may include a light source for generating the first light signal of the first wavelength and the second light signal of the second wavelength and a light source driver for driving the light source. The light source unit may apply the generated first and second light signals to the predetermined part of the subject's body where an arterial pulsating component is measured.

The controller may output the predetermined control signal to the light source unit to sequentially turn on and off the LED array in accordance with the wavelengths to be output.

The photodetecting unit may include a photodetector for detecting the first and second light signals, which are generated by the light source unit and applied to the predetermined part of the subject's body, and for outputting first and second current signals and a current to voltage converter for converting the first and second current electric signals into first and second voltage electric signals.

The diagnosis unit may include a multiplexer for separating the first and second electric signals output from the photodetecting unit according to the predetermined control signal, a delay unit for sampling the separated first and second electric signals and delaying the sampled first and second electric signals for a period of time to output the sampled first and second electric signals at substantially the same time, a divider for calculating a ratio of the sampled first and second electric signals output from the delay unit, and a comparator for comparing the calculated ratio with the predetermined reference value to determine the presence or absence of sleep apnea.

The delay unit may include a sample-and-holder for sampling signals output from the multiplexer and an amplifier for amplifying a signal from the sample-and-holder.

According to another feature of an embodiment of the present invention, there is provided a method of diagnosing sleep apnea, which detects a temporary cessation of breathing while a subject is sleeping by applying light to and processing light output from a predetermined part of the subject's body, the method including (a) sequentially generating a first light signal of a first wavelength and a second light signal of a second wavelength, the first wavelength and the second wavelength being difference, (b) applying the first and second light signals to the predetermined part of the subject's body, (c) detecting the first and second light signals from the predetermined part and converting the first and second light signals into first and second electric signals, (d) sampling the converted first and second electric signals and respectively delaying the sampled first and second electric signals to substantially remove a time difference between the sampled first and second electric signals, and (e) calculating a ratio of the first and second electric signals and comparing the calculated ratio with a predetermined reference value to determine the presence or absence of sleep apnea.

In the method, the first wavelength may be in a red wavelength range and the second wavelength may be in an IR wavelength range.

Applying the first and second light signals may include applying the first and second light signals to the predetermined part of the subject's body where an arterial pulsating component is measured.

In the method, after the ratio of the electric signals, which are sampled in a normal breathing state and a breathing cessation state, is calculated several times, a value from among the calculated ratios is provided as the predetermined reference value.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF THE INVENTION

Korean Patent Application No. 2003-26396, filed on Apr. 25, 2003, in the Korean Intellectual Property Office, and entitled: "Apparatus and Method for Diagnosing Sleep Apnea," is incorporated by reference herein in its entirety.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 1:
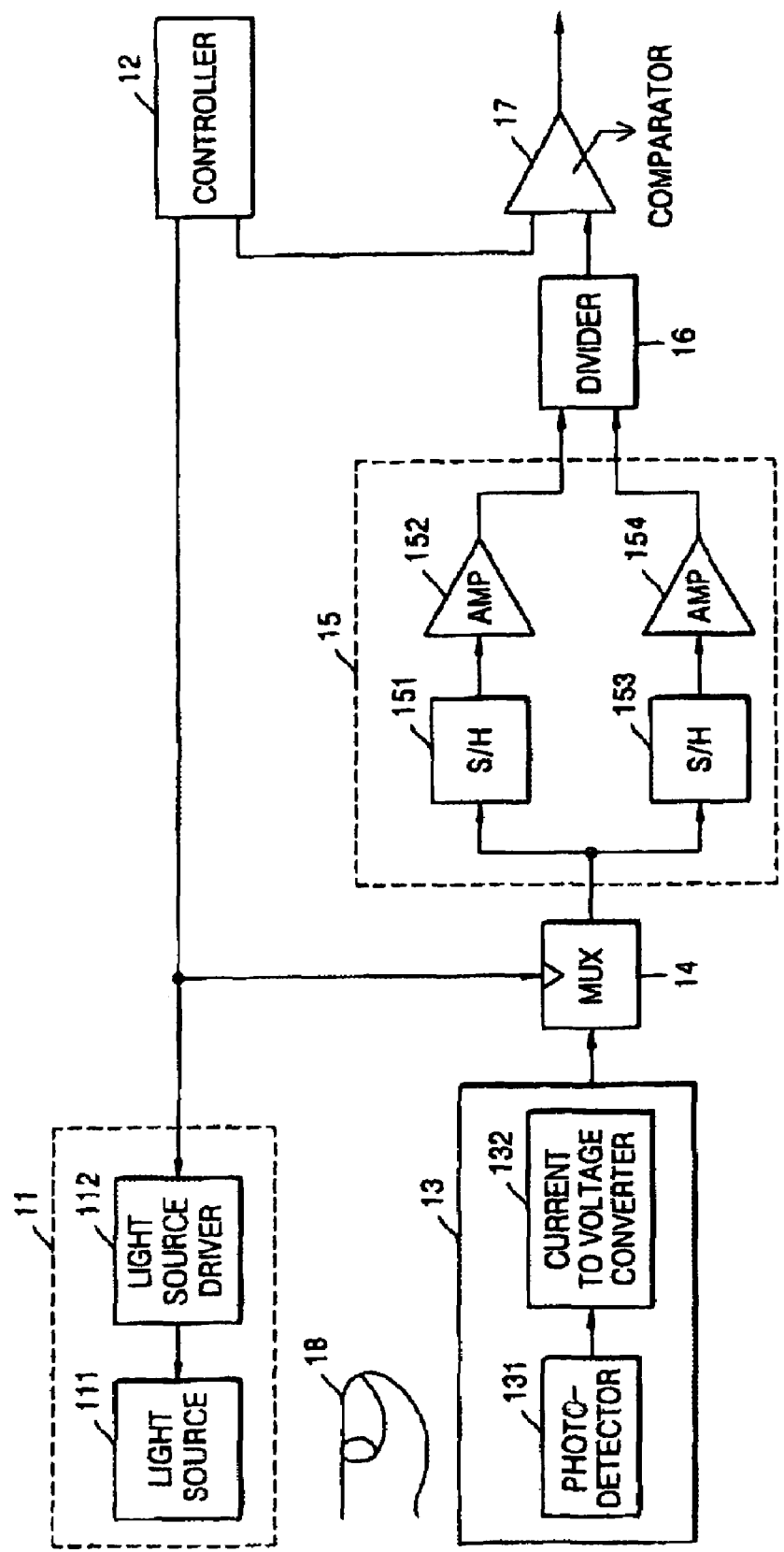
FIG. 1 is a schematic block diagram of an apparatus for diagnosing sleep apnea according to an embodiment of the present invention.

FIG. 1 is a schematic block diagram of an apparatus for diagnosing sleep apnea according to an embodiment of the present invention. As shown in FIG. 1, the sleep apnea diagnosing apparatus includes a light source unit 11, a controller 12, a photodetecting unit 13, a multiplexer (MUX) 14, a delay unit 15, a divider 16, and a comparator 17. The MUX 14, the delay unit 15, the divider 16, and the comparator 17 may be collectively referred to as a diagnostic unit.

The light source unit 11 includes a light source 111, which outputs light in different wavelength ranges, and a light source driver 112, which drives the light source 111.

The photodetecting unit 13 includes a photodetector 131, which converts optical signals generated by the light source 111 into current electric signals, i.e., currents, and a current to voltage (IN) converter 132, which converts the current electric signals into voltage electric signals, i.e., voltages. In connection with the present invention, currents and voltages may be generally referred to as electric signals.

The delay unit 15 includes two sample-and-holders (S/H) 151 and 153, which sample signals output from the MUX 14 and delay the sampled signals for a predetermined period of time, and two amplifiers (AMP) 152 and 154.

The diagnostic unit, i.e., the MUX 14, the delay unit 15, the divider 16, and the comparator 17, processes the voltage electric signals output from the photodetecting unit 13 to determine the presence or absence of sleep apnea.

Operation of the sleep apnea diagnosing apparatus, constructed as described above, will now be explained. In operation, the light source driver 112 drives the light source 111 according to a predetermined control signal from the controller 12. The predetermined control signal indicates whether the light source 111 is to generate a red light or an infrared (IR) light. The light source 111 may be a light emitting diode (LED) array including at least two light emitting diodes that respectively emit light in a red and an IR wavelength range.

The controller 12 outputs the predetermined control signal to sequentially turn on and off the LED array in accordance with the wavelengths to be output.

The light generated by the light source 111 is applied to a predetermined part of a subject's body 18, e.g., a finger, to measure an amount of oxygen in hemoglobin in the blood. The body part 18 may be any body part where an arterial pulsating component can be measured.

The photodetector 131 detects the light signals that are generated by the light source 111 and pass through or are reflected on the body part 18, and outputs currents corresponding to the intensity of the detected light signals. The IN converter 132 converts the current electric signals into voltage electric signals.

The MUX 14 separates the light signals output from the photodetecting unit 13 into red light and IR light according to the wavelengths under the control of the predetermined control signal output from the controller 12.

The delay unit 15 samples voltages of the two light signals, which are separated by and output from the MUX 14, holds each for a predetermined period of time, and amplifies the sampled voltages. This process is done to properly delay the two light signals, which are separately output from the MUX 14 with a time difference therebetween, to remove the time difference and output the two light signals substantially at the same time.

The divider 16 divides the two voltages output from the two amplifiers 152 and 154. The comparator 17 compares a predetermined reference value provided from the controller 12 with a resultant value obtained by the divider 16 to determine whether a subject is experiencing sleep apnea. If it is determined that the subject is experiencing sleep apnea, the controller 12 can send an alarm message to the subject or another person, e.g., a tester, using an additional alarm device (not shown). The comparator 17 and the controller 12 may be wirelessly connected, if necessary, so as not to restrict movement of the subject.

The theory on which the above-described sleep apnea diagnosing apparatus is based will be explained as follows. When breathing temporarily stops, e.g., due to sleep apnea, no oxygen enters the body, and thus oxygen saturation in the blood abnormally decreases. Oxygen saturation is able to be optically measured.

Figure 2:
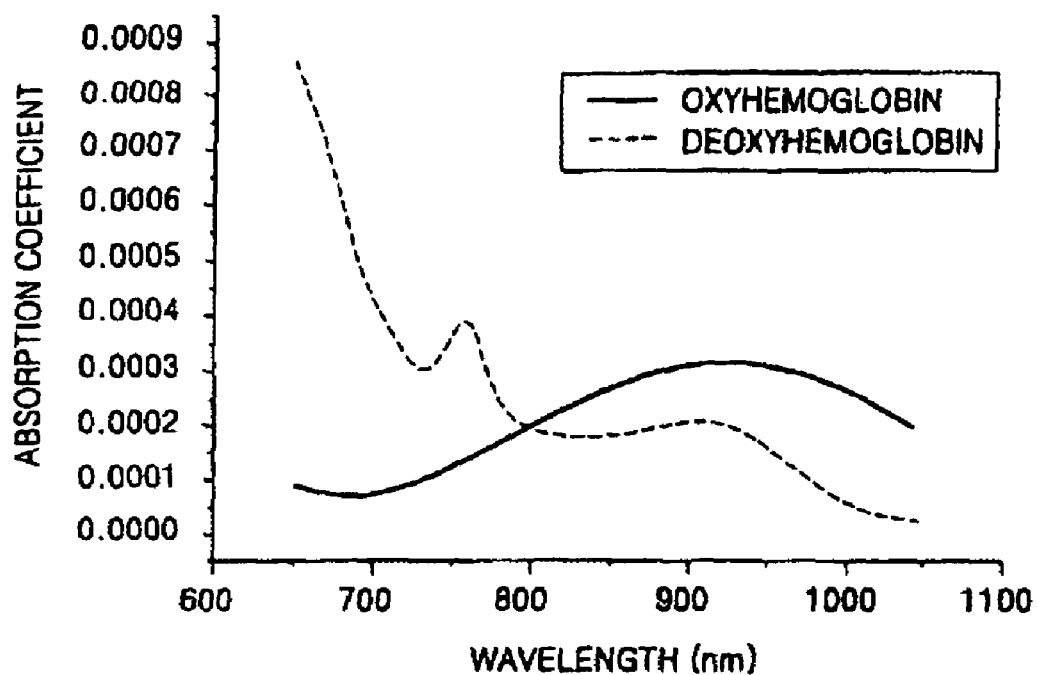
FIG. 2 is a graph illustrating absorption coefficients of oxyhemoglobin and deoxyhemoglobin with respect to wavelength.

FIG. 2 is a graph illustrating absorption coefficients of oxyhemoglobin, i.e., hemoglobin containing oxygen, and deoxyhemoglobin, i.e., hemoglobin without oxygen, with respect to wavelength. As shown in FIG. 2, absorption coefficient curves with respect to wavelength can be entirely different depending on whether hemoglobin in the blood contains oxygen. Therefore, oxygen saturation can be predicted by comparing an amount of a reacted light in a red wavelength range in the body with an amount of a reacted light in an IR wavelength range in the body.

Figure 3:
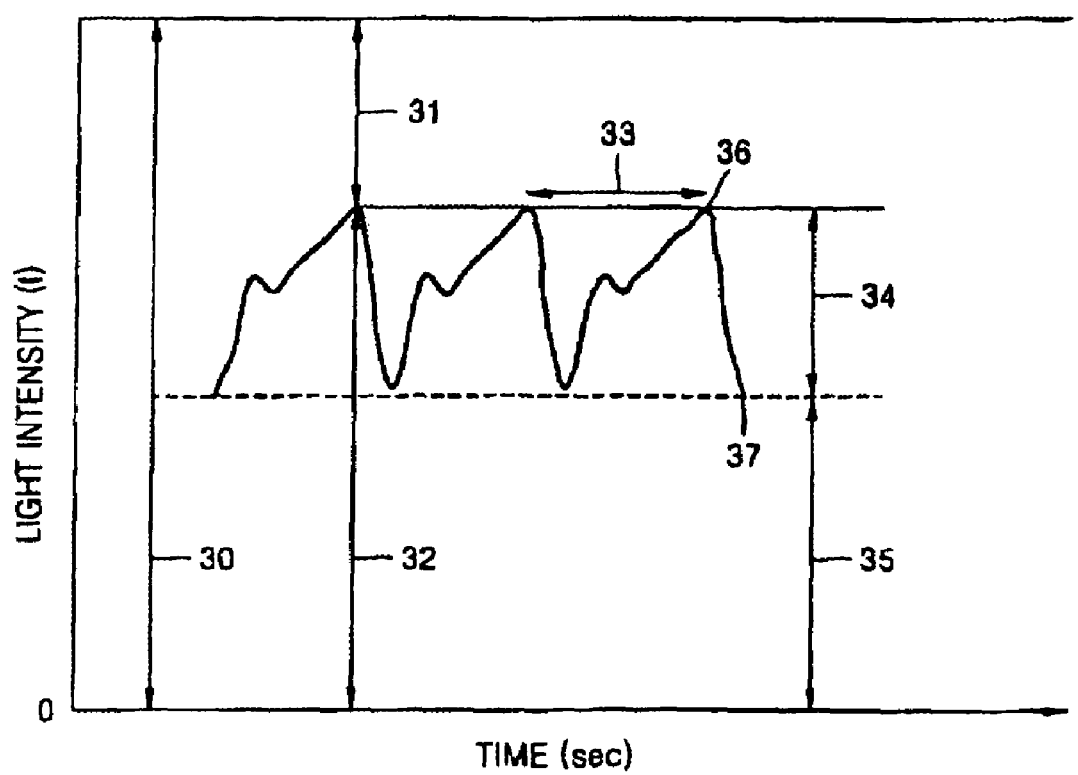
FIG. 3 is a graph illustrating a typical waveform of photoplethysmography (PPG)

When light is applied to a body part to predict the oxygen saturation levels, a photoplethysmography (PPG) waveform, as shown in FIG. 3, is obtained through transmission or reflection of the applied light. In the waveform, reference numeral 30 denotes a quantity of light applied to the body, reference numeral 31 denotes a quantity of absorbed light absorbed by the body, reference numeral 32 denotes a quantity of a light transmitted through the body, reference numeral 33 denotes a cardiac cycle, reference numeral 34 denotes an amount of change in the intensity of the transmitted light due to an arterial pulsating component, i.e., an alternating current (AC) component, reference numeral 35 denotes an amount of change in the intensity of the transmitted light due to an arterial non-pulsating component, i.e., a direct current (DC) component, reference numeral 36 denotes a peak of heartbeat, and reference numeral 37 denotes a valley of heartbeat.

The AC component in the PPG waveform is obtained by measuring a change in blood flow, which reflects a change in a blood stream due to heartbeat. A method of measuring a heart rate using the AC component is widely known. The AC component may be generated by respiration or by a person's voluntary or involuntary movement. At this time, the AC component is non-periodical and weaker in power than that generated due to a heartbeat. The DC component in the PPG waveform is generated when light is absorbed or scattered by a buried object, e.g., bone, skin, or hypodermis, which do not vary with respect to time.

Figure 4:
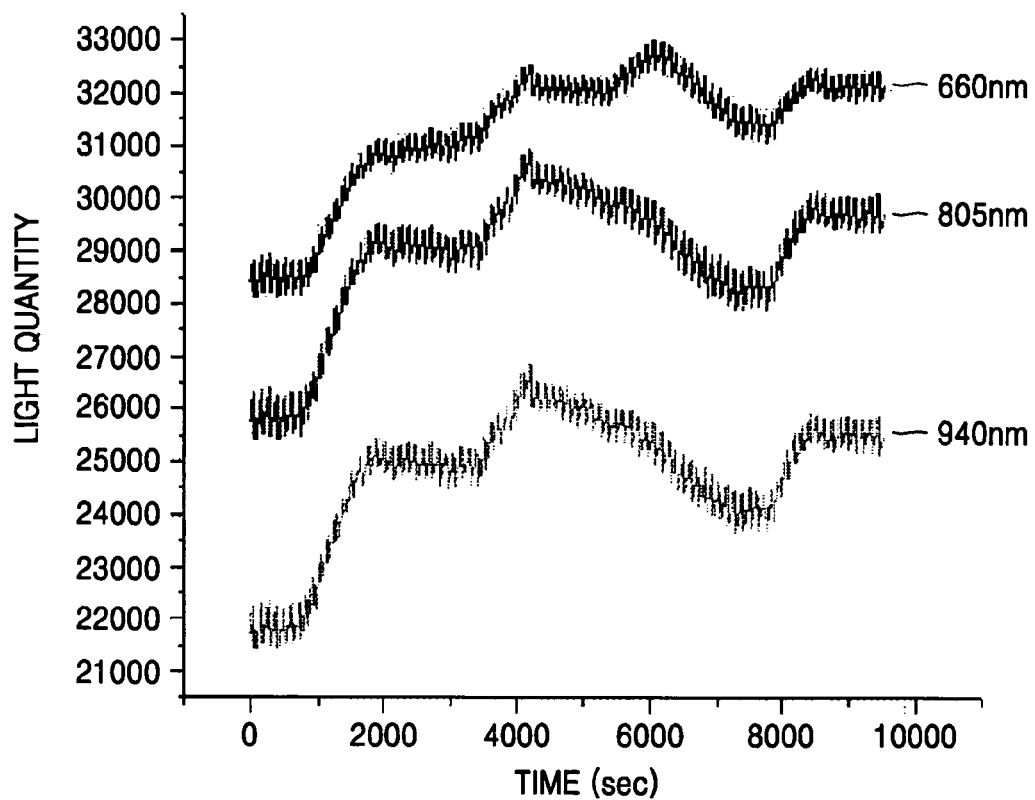
FIG. 4 is a graph illustrating PPG waveforms according to various wavelengths during a normal breathing state.
Figure 5:
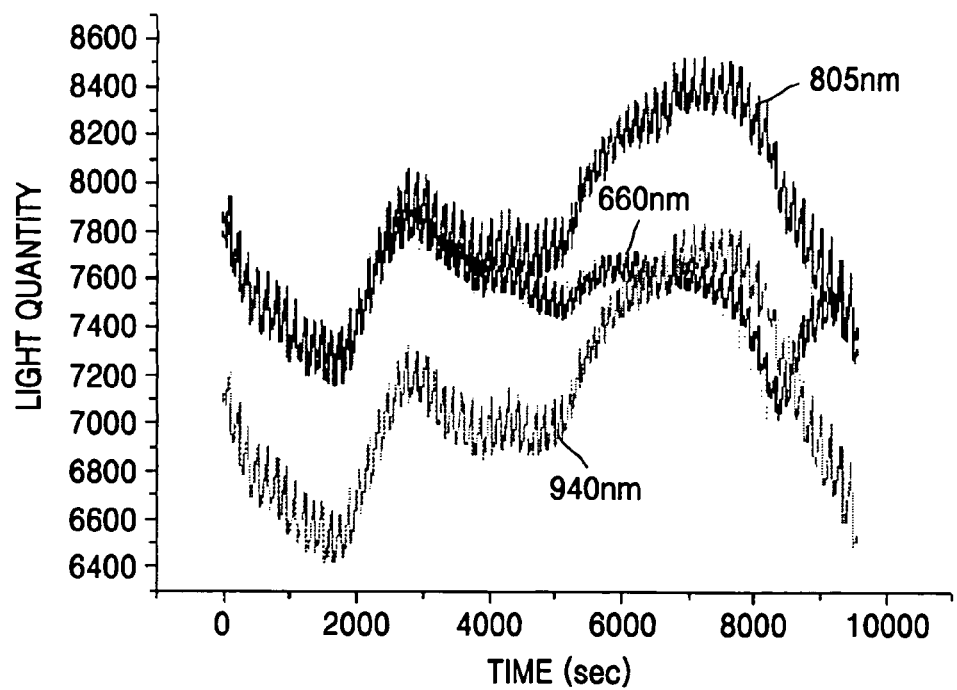
FIG. 5 is a graph illustrating PPG waveforms according to various wavelengths during a breathing cessation state.

When no oxygen is entering the body because of sleep apnea, the amount of deoxyhemoglobin increases. Since an absorption coefficient of deoxyhemoglobin for red light is greater than that for IR light, the red light accordingly becomes more attenuated, as shown in FIG. 2. FIGS. 4 and 5 illustrate PPG waveforms during a normal breathing state and a breathing cessation state, respectively. As shown in FIGS. 4 and 5, during a normal breathing state, similar slope patterns are shown over time. However, during a breathing cessation state, the amount of red light, e.g., having a wavelength of 660 nm, decreases due to an increase in the amount of deoxyhemoglobin.

In general, the DC component in the PPG waveform of FIG. 3 differs significantly depending on a thickness of a finger or characteristics of a particular body part through which light is transmitted. Thus, by taking a transmission ratio between different wavelengths, the difference arising from the characteristics of the particular body part can be eliminated. The present invention uses DC components of red light and IR light output from the MUX 14 and the delay unit 15. The divider 16 divides the DC component of the IR light by the DC component of the red light. The value obtained by the division is referred to as a ratiometric index (RI). The comparator 17 compares the RI with the predetermined reference value provided by the controller 12, and determines that breathing has temporarily ceased during sleep when the output value of the divider 16 is greater than the predetermined reference value.

Figure 6:
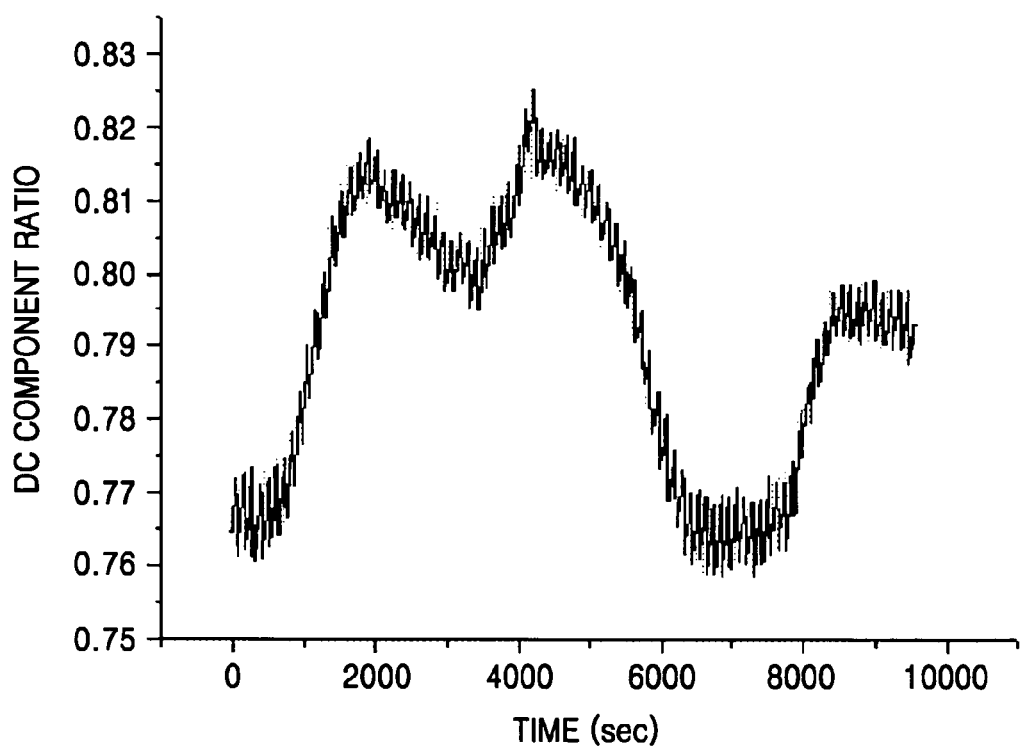
FIG. 6 is a graph illustrating a direct current (DC) component ratio between light in a red wavelength range and an IR wavelength range during a normal breathing state.
Figure 7:
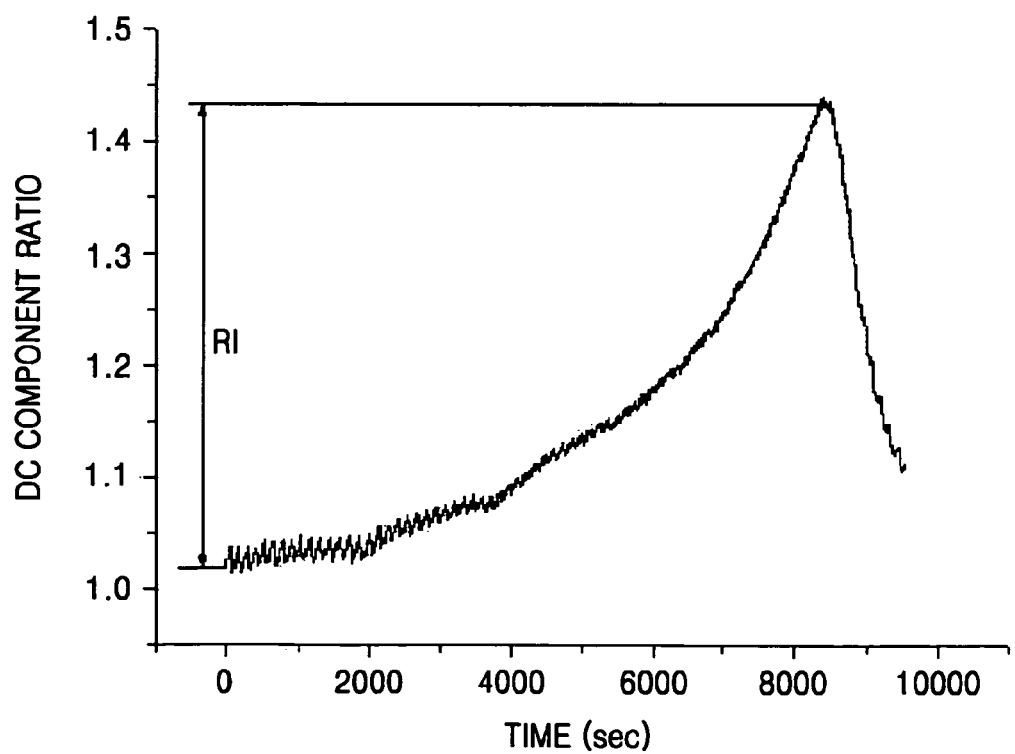
FIG. 7 is a graph illustrating a DC component ratio between light in a red wavelength range and an IR wavelength range during a breathing cessation state.

FIGS. 6 and 7 illustrate a DC component ratio between red light and IR light during a normal breathing state and a breathing cessation state, respectively. Referring to FIGS. 6 and 7, during a normal breathing state, the DC component ratio shows a similar shape to the original light output from the light source unit. During a breathing cessation state, however, the DC component ratio between the two light signals, i.e., the RI, increases over time. As a consequence, when the RI is greater than the predetermined reference value, it is determined that sleep apnea is occurring.

Table 1 shows measurement results of average RIs during a breathing cessation state and a normal breathing state. The measurements were repeatedly taken on six subjects six times per minute. For every minute measurement, the six subjects in the test were allowed to cease their breathing for ten or more seconds three times and breathe normally three times. Two light signals, a first light signal having a red wavelength of 600 nm and a second light signal having an IR wavelength of 940 nm, were utilized.

TABLE 1

| Subject | Average RI during breathing cessation state | Average RI during normal breathing state |
| --- | --- | --- |
| 1 | 0.3 ± 0.03 | 0.024 ± 0.004 |
| 2 | 0.15 ± 0.07 | 0.027 ± 0.01 |
| 3 | 0.49 ± 0.06 | 0.024 ± 0.005 |
| 4 | 0.2 ± 0.05 | 0.029 ± 0.009 |
| 5 | 0.32 ± 0.05 | 0.03 ± 0.008 |
| 6 | 0.14 ± 0.03 | 0.035 ± 0.009 |

Here, an RI in data measured when breathing has stopped for ten or more seconds ranges from 0.096 to 0.56. An RI in data measured when breathing is normal ranges from 0.02 to 0.07. It is preferable that a value in a range from 0.07 to 0.096 is adopted as the predetermined reference value for use by the comparator 17. In other words, after the RI in data measured when breathing has stopped and the RI in data measured when breathing is normal has been calculated several times, a value from among the calculated ratios is provided as the predetermined reference value.

Conventionally, when there is data where any peak value cannot be found in a PPG waveform affected by noise due to respiration or movement, the data is reflected in the prediction of oxygen saturation. When sleep apnea is diagnosed based on that predicted oxygen saturation, the predictions result in errors.

Table 2 shows a difference between a predicted value of oxygen saturation and a measured value when the six subjects intentionally made noise three times by moving their bodies.

TABLE 2

| Subject | Average error (%) |
|---------|-------------------|
| 1 | 9.7 ± 1.2 |
| 2 | 5.7 ± 0.6 |
| 3 | 6 ± 0.06 |
| 4 | 1.3 ± 0.6 |
| 5 | 3 ± 0.5 |
| 6 | 3.7 ± 0.6 |

According to Table 2, since the present invention uses the DC component ratio instead of peak and valley values in the AC component, it is not affected by noise due to movement when diagnosing sleep apnea.

As may be seen from the above description, the present invention is able to diagnose sleep apnea at a subject's home irrespective of the causes of the sleep apnea or the type of sleep apnea. Furthermore, contrary to conventional systems, the present invention is able to measure the RI without being affected by noise from voluntary or involuntary movement generated during sleep.

Reflection- or transmission-type PPG waveforms are measured with relative ease, such that they can be measured using any body part, e.g., a finger, toe, wrist, or a crown of an infant's head.

Since a conventional breathing cessation detector or an impedance change detector employing a method of measuring oxygen saturation levels uses an analog to digital (A/D) converter, it requires a high performance microcontroller. However, since the present invention uses analog hardware without an A/D converter, it can be realized in a low performance microcontroller.

A conventional PPG for measuring oxygen saturation is required to detect both peak and valley values of an AC component. In this process, errors can occur in the detected results because of internal and external parameters including a subject's movement and respiration. However, the present invention uses the DC value in the PPG, such that it is relatively less susceptible to noise, and DC varying factors of low frequency can be eliminated by the measurement of a ratio between two light signals.

Exemplary embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. An apparatus for diagnosing sleep apnea, which detects a temporary cessation of breathing while a subject is sleeping by applying light to and processing light output from a predetermined part of a subject's body, the apparatus comprising:

a light source unit for sequentially generating a first light signal of a first wavelength and a second light signal of a second wavelength according to a predetermined control signal, the first wavelength and the second wavelength being different;

a photodetecting unit for detecting the first and second light signals output by the light source unit and then applied to the predetermined part of the subject's body, and for converting the detected first and second light signals into first and second electric signals;

a diagnosis unit for substantially removing a time delay between the first and second electric signals output from the photodetecting unit, for calculating a ratio of DC components of the first and second electric signals, and for comparing the ratio with a predetermined reference value to diagnose sleep apnea; and a controller for outputting the predetermined control signal to the light source unit to generate the first and second light signals, and for providing the predetermined reference value to the diagnosis unit.

2. The apparatus as claimed in claim 1, wherein the light source unit is a light emitting diode (LED) array that generates light in at least a red wavelength range and an infrared (IR) wavelength range.

3. The apparatus as claimed in claim 2, wherein the light source unit comprises:

a light source for generating the first light signal of the first wavelength and the second light signal of the second wavelength; and a light source driver for driving the light source.

4. The apparatus as claimed in claim 2, wherein the light source unit is configured to apply the generated first and second light signals to a predetermined part of the subject's body where an arterial pulsating component can be measured.

5. The apparatus as claimed in claim 2, wherein the controller outputs the predetermined control signal to the light source unit to sequentially turn on and off the LED array in accordance with the wavelengths to be output.

6. The apparatus as claimed in claim 1, wherein the photodetecting unit comprises:

a photodetector for detecting the first and second light signals, which are generated by the light source unit and applied to the predetermined part of the subject's body, and for outputting first and second current signals; and a current to voltage converter for converting the first and second current electric signals into first and second voltage electric signals.

7. The apparatus as claimed in claim 6, wherein the diagnosis unit comprises:

a multiplexer for separating the first and second electric signals output from the photodetecting unit according to the predetermined control signal;

a delay unit for sampling the separated first and second electric signals and delaying the sampled first and second electric signals for a period of time to output the sampled first and second electric signals at substantially the same time;

a divider for calculating a ratio of DC components of the sampled first and second electric signals output from the delay unit; and a comparator for comparing the calculated ratio with the predetermined reference value to determine the presence or absence of sleep apnea.

8. The apparatus as claimed in claim 7, wherein the delay unit comprises:
   a sample-and-holder for sampling signals output from the multiplexer; and
   an amplifier for amplifying a signal from the sample-and-holder.

9. The apparatus as claimed in claim 1, wherein the diagnosis unit comprises:
   a multiplexer for separating the first and second electric signals output from the photodetecting unit according to the predetermined control signal;
   a delay unit for sampling the separated first and second electric signals and delaying the sampled first and second electric signals for a period of time to output the sampled first and second electric signals at substantially the same time;
   a divider for calculating a ratio of DC components of the sampled first and second electric signals output from the delay unit; and
   a comparator for comparing the calculated ratio with the predetermined reference value to determine the presence or absence of sleep apnea.

10. The apparatus as claimed in claim 9, wherein the delay unit comprises:
   a sample-and-holder for sampling signals output from the multiplexer; and
   an amplifier for amplifying a signal from the sample-and-holder.

11. The apparatus as claimed in claim 1, wherein the first electric signal corresponds to a detected red light signal,
   the second electric signal corresponds to a detected infrared light signal, and
   the ratio of DC components of the first and second electric signals is one of: ($DC_{IR}/DC_{red}$) and ($DC_{red}/DC_{IR}$), where $DC_{red}$ is a DC component of the first electric signal and $DC_{IR}$ is a DC component the second electric signal.

12. A method of diagnosing sleep apnea, which detects a temporary cessation of breathing while a subject is sleeping by applying light to and processing light output from a predetermined part of the subject's body, the method comprising:
   (a) sequentially generating a first light signal of a first wavelength and a second light signal of a second wavelength, the first wavelength and the second wavelength being different;
   (b) applying the first and second light signals to the predetermined part of the subject's body;
   (c) detecting the first and second light signals from the predetermined part and converting the first and second light signals into first and second electric signals;
   (d) sampling the converted first and second electric signals and respectively delaying the sampled first and second electric signals to substantially remove a time difference between the sampled first and second electric signals; and
   (e) calculating a ratio of DC components of the first and second electric signals and comparing the calculated ratio with a predetermined reference value to determine the presence or absence of sleep apnea.

13. The method as claimed in claim 12, wherein the first wavelength is in a red wavelength range and the second wavelength is in an IR wavelength range.

14. The method as claimed in claim 12, wherein applying the first and second light signals comprises applying the first and second light signals to a predetermined part of the subject's body where an arterial pulsating component can be measured.

15. The method as claimed in claim 13, wherein the first electric signal corresponds to a detected red light signal,
   the second electric signal corresponds to a detected infrared light signal, and
   the ratio of DC components of the first and second electric signals is one of: ($DC_{IR}/DC_{red}$) and ($DC_{red}/DC_{IR}$), where $DC_{red}$ is a DC component of the first electric signal and $DC_{IR}$ is a DC component the second electric signal.

16. The method as claimed in claim 15, wherein the predetermined reference value is one of: a predetermined ratio of ($DC_{IR}/DC_{red}$) and a predetermined ratio of ($DC_{red}/DC_{IR}$).

17. The method as claimed in claim 12, wherein applying the first and second light signals comprises applying the first and second light signals to a predetermined part of the subject's body where an arterial pulsating component can be measured.

18. The method as claimed in claim 12, wherein the predetermined reference value is a predetermined ratio of DC components of the electric signals.

19. The method as claimed in claim 12, wherein the predetermined reference value is a predetermined ratio of DC components of the first and second electric signals.

* * * * *